(12) United States Patent
Coury et al.

(10) Patent No.: US 10,766,995 B2
(45) Date of Patent: Sep. 8, 2020

(54) POLYURETHANES

(71) Applicant: STRAIT ACCESS TECHNOLOGIES HOLDINGS (PTY) LTD, Observatory, Cape Town (ZA)

(72) Inventors: Arthur Coury, Boston, MA (US);
Deon Bezuidenhout, Cape Town (ZA);
Jandré De Villiers, Kuilsriver (ZA);
Johan Coetzee, Cape Town (ZA);
David Gideon Conradie, Cape Town (ZA)

(73) Assignee: Strait Access Technologies Holdings (Pty) Ltd., Cape Town (ZA)

( * ) Notice: Subject to any disclaimer, the term of this patent is extended or adjusted under 35 U.S.C. 154(b) by 0 days.

(21) Appl. No.: 15/537,386

(22) PCT Filed: Dec. 18, 2015

(86) PCT No.: PCT/IB2015/059787
§ 371 (c)(1),
(2) Date: Jun. 16, 2017

(87) PCT Pub. No.: WO2016/098073
PCT Pub. Date: Jun. 23, 2016

(65) Prior Publication Data
US 2018/0016380 A1  Jan. 18, 2018

(30) Foreign Application Priority Data
Dec. 19, 2014  (ZA) .................... 2014/09373

(51) Int. Cl.
*A61L 27/18* (2006.01)
*A61L 27/50* (2006.01)
(Continued)

(52) U.S. Cl.
CPC .......... *C08G 18/3206* (2013.01); *A61L 27/18* (2013.01); *A61L 27/507* (2013.01);
(Continued)

(58) Field of Classification Search
CPC ............ C08G 18/7671; C08G 18/6208; C08G 18/3206; C08G 18/3228; C08G 18/3234; C08G 18/3271; C08G 18/328
See application file for complete search history.

(56) References Cited

U.S. PATENT DOCUMENTS 4,791,168 A    12/1988  Salatin et al.
5,254,662 A *  10/1993  Szycher .................. A61L 27/18
                                                                  528/67
(Continued)

FOREIGN PATENT DOCUMENTS

CN    1 919 890 A      2/2007
CN    101868487        10/2010
(Continued)

OTHER PUBLICATIONS

International Search Report of International Application No. PCT/IB2015/059787, filed Dec. 18, 12015, dated Aug. 1, 2016 in 6 pages.
(Continued)

*Primary Examiner* — Michael L Leonard
(74) *Attorney, Agent, or Firm* — Knobbe Martens Olson & Bear LLP

(57) ABSTRACT

Partially crosslinked polyurethane polymers comprising diisocyanates and aliphatic hydrocarbon soft segments with a short-chain diol chain extender and a multifunctional amine and/or alcohol crosslinker to provide a polyurethane polymer with useful properties for the production of medical implant devices such as heart valves, are described. The polymers have an unexpected linear elastic region in a range from 5-100% and preferably between 10-35%. In some
(Continued)

embodiments the polyurethanes are a thermally convertible gel formulation which may be converted to a liquid formulation by extended heating to render the polymer suitable for solvent processing techniques such as casting, spraying, spinning, etc. The invention also provides for living hinge polyurethane polymers which are thermally modifiable from a gel to a liquid and reaction injection moulded (RIM) polyurethanes with an enhanced flex life.

10 Claims, 9 Drawing Sheets

(51) Int. Cl.
 *C08G 18/62* (2006.01)
 *C08G 18/32* (2006.01)
 *C08G 18/48* (2006.01)
 *C08G 18/76* (2006.01)
 *C08G 18/75* (2006.01)
 *C08G 18/66* (2006.01)

(52) U.S. Cl.
 CPC ....... *C08G 18/329* (2013.01); *C08G 18/3212* (2013.01); *C08G 18/3228* (2013.01); *C08G 18/3234* (2013.01); *C08G 18/3243* (2013.01); *C08G 18/3246* (2013.01); *C08G 18/3271* (2013.01); *C08G 18/3281* (2013.01); *C08G 18/3284* (2013.01); *C08G 18/4854* (2013.01); *C08G 18/4858* (2013.01); *C08G 18/6208* (2013.01); *C08G 18/6674* (2013.01); *C08G 18/6685* (2013.01); *C08G 18/6688* (2013.01); *C08G 18/751* (2013.01); *C08G 18/755* (2013.01); *C08G 18/758* (2013.01); *C08G 18/765* (2013.01); *C08G 18/7621* (2013.01); *C08G 18/7671* (2013.01); *A61L 2430/20* (2013.01)

(56) References Cited

U.S. PATENT DOCUMENTS

| | | | | |
|---|---|---|---|---|
| 5,589,563 | A | * | 12/1996 | Ward .................. A61L 27/18 210/500.21 |
| 5,864,001 | A | * | 1/1999 | Masse ................... C08G 18/10 528/75 |
| 6,066,436 | A | | 5/2000 | Kumpfmiller et al. |
| 6,111,049 | A | * | 8/2000 | Sendijarevic ......... C08G 18/10 528/59 |
| 2010/0056682 | A1 | | 3/2010 | Meltzer et al. |
| 2011/0098417 | A1 | | 4/2011 | Worley et al. |

FOREIGN PATENT DOCUMENTS

| | | | | |
|---|---|---|---|---|
| EP | | 624612 A1 | * 11/1994 | ............ C08G 18/62 |
| WO | WO 2009/039145 | | 3/2009 | |

OTHER PUBLICATIONS

Written Opinion of International Application No. PCT/IB2015/059787, filed Dec. 18, 2015, dated Aug. 1, 2016 in 11 pages.
Office Action received in Chinese Application No. 201580076625.9, dated Nov. 6, 2019.

\* cited by examiner

POLYURETHANES

CROSS-REFERENCE(S) TO RELATED APPLICATIONS

This application is the U.S. National Phase under 35 U.S.C. § 371 of International Application No. PCT/IB2015/059787, filed Dec. 18, 2015, designating the U.S., and published in English as WO 2016/098073 A2 on Jun. 23, 2016, which claims priority to South African Provisional Patent Application No. 2014/09373, filed Dec. 19, 2014, the entire contents of which are incorporated herein by reference.

FIELD OF THE INVENTION

This invention relates to polyurethane formulations, including linear and crosslinked polyurethanes, more particularly polyurethanes for use in medical implant devices and methods of manufacture of such polyurethanes.

BACKGROUND TO THE INVENTION

Polyurethanes (PUs) have been extensively studied for use in medical applications such as pacemaker leads, blood bags, catheters, bladders, artificial hearts, vascular grafts and synthetic heart valves.

Although there are a number of formulations offering a great variety of chemical and physical properties, they are mostly thermoplastic compositions and there remain two major drawbacks of PUs used in medical applications: they are susceptible to certain conditions that can cause chemical degradation of properties in vivo and they may be prone to excessive strain relaxation (creep) especially where cyclic stress is incurred, such as in cardiovascular prostheses.

There have been a number of attempts to improve the chemical and mechanical properties of PUs. As the chemical stability of PUs is closely linked to the chemical nature of the macroglycol units constituting soft segments of PUs, the polyester macroglycols initially used and found to be hydrolytically unstable in vivo, were replaced with soft segments based on polyethers. However, subsequent studies showed that although the polyether segments were hydrolytically stable, certain polyether urethanes were susceptible to oxidative degradation in the presence of metal ions and other strong oxidants present in physiological media. Further studies toward full or partial replacement of the polyether functionalities with carbonates, siloxanes, hydrocarbons and fluorinated ethers continue.

The use of polycarbonate soft segments has been reported to increase chemical stability, but have been shown to still be susceptible to hydrolytic and oxidative degradation. Although siloxane based polyurethane materials were initially thought to be both hydrolytically and oxidatively stable, they have also recently been shown to degrade in aqueous media. Siloxane soft segment-based PUs also tend to have lower toughness than their polyether soft-segment counterparts. Medtronic Inc. (U.S. Pat. No. 4,873,308) eliminated the use of polyester, polyether and polycarbonates by basing an experimental urethane on hydrocarbon (dimerol) soft segments. Dimerols are derived from dimer acids: The dimer acids as the term is used herein are described and discussed in the book "The Dimer Acids", edited by Edward C. Leonard, published by Humko Sheffield Chemical, 1975. Dimer acids are the reaction product of a Diels-Alder addition or other coupling process of two aliphatic, unsaturated, predominantly 18 carbon fatty acids. Dimer acids take the form of single ring, double ring or branched chain structures predominantly having two carboxylic acid functionalities. This modification indeed produced enhanced biostability, but being uncrosslinked polymers, they would still be prone to significant plastic deformation.

In this specification, "living hinge" is defined as a polymer which induces a yield strain in the hinge zone. A yield point can be defined as an increase in strain without a corresponding increase in stress. It is an initial extension of the polymer specimen beyond its elastic limit and this results in an alignment of the polymer molecules in the hinge which gives enhanced flex life. It results in a necking down relative to the thickness of the specimen on either side. The patent by Moe (U.S. Pat. No. 6,117,169) which generally discloses a heart valve having a living hinge attachment describes heart valves where the valve cusps are integral with the valve sheath and thus appears to be different from this definition. Silicone polymers sometimes described in synthetic valve designs, (Reference V. M. Parfeev, I. V. Grushetskii, E. V. Smurova: "Mechanical Properties of Elastomers for Artificial Leaflet Heart Valves," Mechanics of Composite Materials, January-February, 1983, Volume 19, Issue 1, pp 92-99) generally do not have a true yield point and it is also uncommon for polyurethanes to have one.

There is thus a need for chemically and mechanically stable linear and crosslinked polyurethane polymers for use as medical implant devices that alleviate some of the above mentioned problems.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with a first aspect of this invention there is provided a partially crosslinked polyurethane polymer comprising methylene diphenyl diisocyanate (MDI) and an aliphatic hydrocarbon soft segment with a diol chain extender selected from one or more of a butane diol (BDO) and other short-chain diol chain extenders and a crosslinker selected from one or more of a multifunctional amine and alcohol crosslinker.

Further features of this first aspect provide for a polyurethane polymer with a 100% secant modulus in the range of 4 to 15 MPa, an ultimate tensile strength in the range of 2-25 MPa, with a maximum strain of 350-600% and a toughness of 25-60 J/m$^3$.

Still further features of this first aspect of the invention provide for the aliphatic hydrocarbon soft segment to be a hydrogenated polybutadiene diol (HPBD) having a functionality of ~1.9 to 2.2 and a number average molecular weight of ~2000-3000, and for the multifunctional crosslinker to be triethanolamine (TEOA) or trimethylol propane (TMP) in the range of 3 to 15% of the polymer (based on diisocyanate equivalents).

Yet further features of this first aspect of the invention provide for the partially crosslinked polymer to be produced in a solvent system comprising a 4:1 mixture of toluene/DMF or a 1:1 mixture of DMAc/Toluene.

In accordance with a second aspect of this invention there is provided a polyurethane polymer which has a linear elastic region in a range from 5-100%, preferably between 10-60%, specifically between 10-35%. The polyurethane polymer may be crosslinked, partially crosslinked or not crosslinked.

In accordance with a third aspect of this invention there is provided a polyurethane which is formed by reacting an aliphatic, hydrocarbon soft segment with MDI in a two-step process followed by the addition of an diamine, which may be selected from an alkyl, aryl, alkenyl or alkynyl dimaine, such as but not limited to hexamethylene diamine (NMDA), ethylene diamine (EDA), butane diamine (BDA), trimethyl hexamethylene diamine (TMDA), 4,4'-methylenebis(2-chloroaniline) (MOCA), dimeryl diamine and hydrogenated methylene dianiline (MDAH).

Further features of this third aspect provide for the polyurethane to be dissolved in a 1:1 mixture of ortho-dichlorobenzene:N-methyl-2-pyrrolidone (NMP).

In a preferred embodiment of this second aspect of the invention, there is provided a polyurethane having an ultimate tensile strength of 18 MPa with a 50% secant modulus of 4.7 MPa.

In accordance with a fourth aspect of the invention there is provided a polyurethane which is formed by reacting an aliphatic, hydrocarbon soft segment with MDI followed by the addition of an alkanolamine, such as but not limited to, ethanolamine, 3-amino-1-propanol, 4-amino-1-butanol, 4-amino-phenol, as chain extender dissolved in an appropriate solvent system.

Further features of this fourth aspect of the invention provide for the polyurethane to be formed by a one or two-step process; preferably for the polymer to also include a diol chain extender; preferably for the polymer to include a diamine or multifunctional chain extender and preferably one or more of a multifunctional amine and alcohol crosslinker.

In accordance with a fifth aspect of the invention there is provided a polyurethane polymer having a thermally convertible gel formulation which may be converted to a liquid formulation by extended heating to render the polymer suitable for solvent processing techniques.

Further features provide for the solvent processing techniques to be selected from the group comprising casting, spraying, spinning, etc. In a preferred embodiment, the polymer exhibits an ultimate tensile strength of 20 to 60 MPa and a Young's modulus of 10 to 90 MPa.

Further features of this fifth aspect of the invention provide for the polymer to be formed by a one or two-step process; preferably for the polymer to include a diamine or multifunctional chain extender; and for the conversion of the gel to the liquid to be done at a temperature range of 90-125° C.

In accordance with a sixth aspect of the invention there is provided a living hinge polyurethane polymer comprising methylene diphenyl diisocyanate (MDI) and a dimer diol.

Further features provide for the living hinge polymer to have a defined yield point in the range of 10-40 MPa, preferably 20-30 MPa at a strain of 1-10%, preferably 3-7% with an ultimate tensile strength of 20-60 MPa, preferably 30-60 MPa (e.g. 39 MPa at 75% strain) to 40-70 MPa (at 390% strain) and a Young's modulus in the range of 90 MPa to 700 MPa.

Further features of this sixth aspect of the invention provide for the polymer to be crosslinked with one or more of a tri- or higher polyol, or through allophanates and/or biurets in that it has a hard to soft segment ratio of 20 to 80%, preferably 30-70% and more preferably 40-60% (based on equivalents) and a crosslinking of 0-25%, preferably 5-20%, more preferably 5-15% (based on diisocyanate equivalents).

Further features of this sixth aspect of the invention provide for the polymer to be synthesized in a one or two-step process, for the two-step process to be carried out in a suitable solvent or in the molten prepolymer; and for the stoichiometry of the reaction to be selected such that all reactive isocyanate (NCO) groups are reacted.

Suitable solvents may be selected from the group comprising dimethyl acetamide (DMAc), toluene, dimethylformamide (DMF), ortho-dichlorodibenzene, N-methyl-2-pyrrolidone (NMP), methyl ethyl ketone (MEK), dioxane and suitable mixtures thereof; preferably DMAc, mixtures of ortho-dichlorobenzene and NMP, and mixtures of toluene and DMF. The polyurethane may further optionally contain one or more of diamine or diol chain extenders and/or crosslinkers.

Yet further features of the invention provide for the living hinge polyurethane/solvent mixture to be thermally modifiable from a gel to a liquid.

In accordance with a seventh aspect of the invention there is provided a reaction injection moulded (RIM) polyurethane comprising a first component comprising an MDI diisocyanate and polytetramethylene ether glycol (PTMEG), optionally mixed with one or more of catalysts, plasticizers, bulking agents and diluents, and a second component comprising a combination of BDO, other short-chain diols and a crosslinker, such as but not limited to trimethylol propane (TMP) or other polyols, allowing significant crosslinking and enhanced flex life of the polyurethane.

In a preferred embodiment the RIM polyurethane comprises PTMEG and MDI which are mixed at a reaction temperature of 50° C. to form a prepolymer, wherein the prepolymer is added to a mixture of BDO and TMP; and the RIM polyurethane forms a heart valve having an enhanced flex life.

In accordance with a eighth aspect of the invention there is provided a heart valve formed from a RIM polyurethane as described above which has an enhanced flex life.

Embodiments of the invention will now be described, by way of example only, with reference to the accompanying Figures.

DETAILED DESCRIPTION

Figure 1:
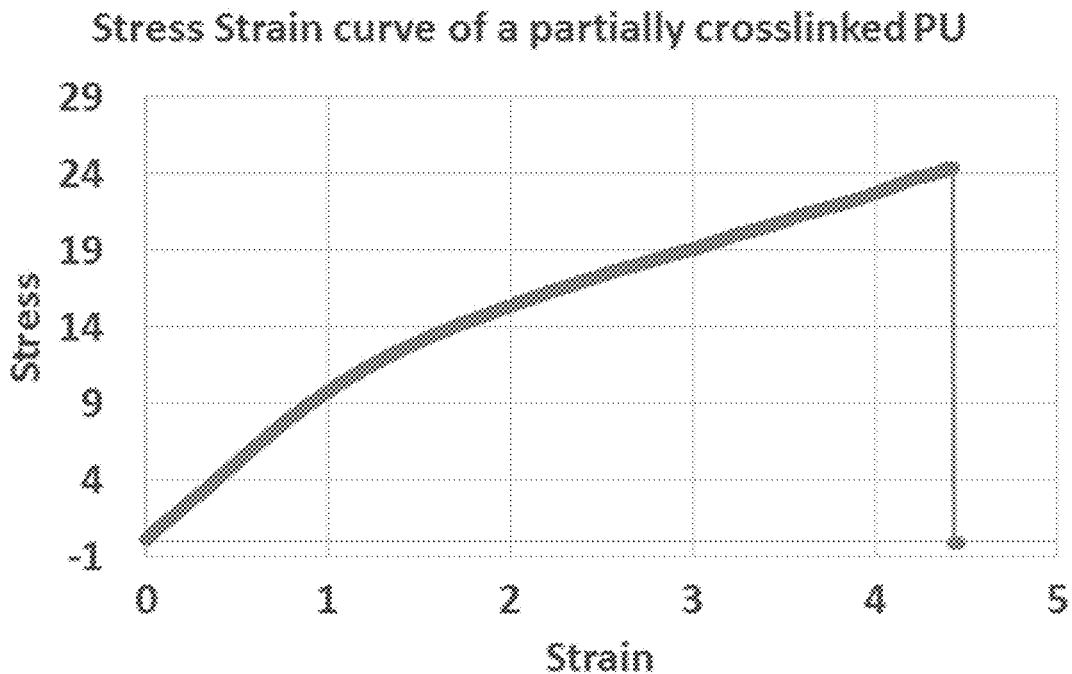
FIG. 1 is a stress strain graph of a partially crosslinked polyurethane sample (Example 1)

A polyurethane (PU) is a polymer containing urethane (also called carbamate) groups. A simple polyurethane can be made by reacting a diisocyanate (DI) with a diol to form a polymer containing urethane groups: (underlined).

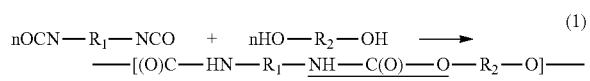
(1)

A segmented PU is a polymer that can be made to be elastic (a thermoplastic elastomer) by performing the above reaction with an oligomeric or polymeric diol: HO—$R_2$—OH (wherein the $R_2$ is an ester/ether/siloxane/hydrocarbon group and referred to as a soft segment) and an excess of DI, e.g.:

$$2nOCN-R_1-NCO+nHO-R_2OH \rightarrow -OCN-[-R_1-NH-C(O)-O-R_2-O-C(O)-HN-]_x-R_1NCO- \quad (2)$$

and subsequently with a diol (normally a short monomeric diol like butanediol ((BDO): HO—$R_3$—OH) to yield:

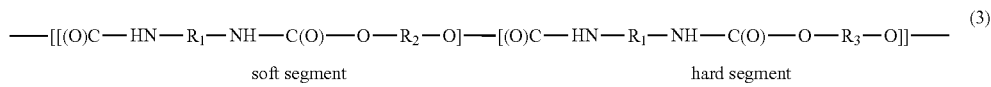
(3)

Phase separation occurs in which the hard segments associate to form virtual crosslinks between the soft segments, which imparts elastomeric properties to the PU. Virtual crosslinking is referred to in this specification as "crosslinking type 1".

The above two-step process (involving steps 2 and 3) can be replaced by a so-called one-step or one-pot process, where the three components are reacted in one pot (simultaneously rather than consecutively). The same process can be applied to extension with diamines, as described below.

When diamines ($H_2N-R_4-NH_2$) are used to extend a prepolymer, a polyurethane urea (PUU) is formed (as it contains both urethane and urea bonds), as shown in (4) below:

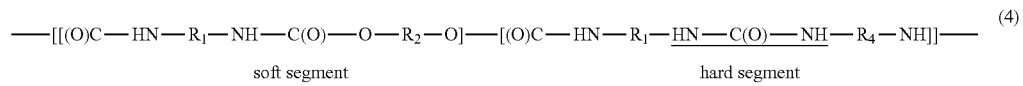
(4)

The reaction of isocyanates with amines is much faster than that with alcohols.

Urea groups generally form stronger virtual crosslinks (through hydrogen bonding) than urethanes, and often give stronger mechanical properties. (NH . . . N=13 kJ/mol> NH . . . O=8 kJ/mol).

Free isocyanate, however, can also react with the carbamate and urea nitrogen to form allophanate and biuret respectively. These side reactions can cause covalent crosslinking of the material (referred to in this specification as "crosslinking type 2"). This can be beneficial as it adds strength but does provide limitations such as with post-reaction processability.

A third way of crosslinking (referred to herein as "crosslinking type 3") involves the use of tri- or multifunctional alcohols or amines, i.e. $R_5-(OH)_n$ or $R_6-(NH_2)_n$ with n=3, 4, 5 etc. If these are used instead of $R_3$ and/or $R_4$ (or in sufficiently large amounts) extensive crosslinking of the polymer ensues. If only a relatively small amount of $R_5$ and/or $R_6$ is used in conjunction with $R_3$ and/or $R_4$, partial or light crosslinking results.

E.g. with a triol crosslinker:

$$—\{[XX]—[(O)C—HN—R_1—NH—C(O)—O—R_3—O]—[(O)—C—HN—R_1—NH—C(O)—O—R_5—O]\}— \quad (5)$$

$$\begin{array}{c} | \\ O \\ \S \\ O \\ | \end{array} \text{ with}$$

$$—\{[XX]—[(O)C—HN—R_1—NH—C(O)—O—R_3—O]—[(O)—C—HN—R_1—NH—C(O)—O—R_5—O]\}—$$

$$XX = —[[(O)C—HN—R_1—NH—C(O)—O—R_2—O]— \quad (6)$$

or with triamine crosslinker:

$$—\{[XX]—[(O)C—HN—R_1—HN—C(O)—NH—R_4—NH]—[(O)—C—HN—R_1—NH—C(O)—HN—R_6—NH]\}— \quad (7)$$

$$\begin{array}{c} | \\ NH \\ \S \\ NH \\ | \end{array}$$

$$—\{[XX]—[(O)C—HN—R_1—HN—C(O)—NH—R_4—NH]—[(O)—C—HN—R_1—NH—C(O)—HN—R_6—NH]\}—$$

Where: § represents the crosslink between the shown chains. The crosslink can also be formed by the section indicated by "XX".

This is "crosslinking type 3", wherein the crosslinking moiety can itself be an isocyanate end-capped polymer chain or monomeric diisocyanate (that has reacted with the third (or 4$^{th}$, 5$^{th}$ etc.) hydroxyl or amine group of the crosslinker by urethane or urea linkages respectively.

Note: the crosslink is connected to the main chains via urethane, urea, allophanate or biuret linkages. Termination of the linear, branched or crosslinked polymers is by isocyanate, hydroxyl or amino functions, preferably the latter two groups.

When alkanolamines ($H_2N—R_7—OH$) are used to extend a prepolymer a polyurethane urea is also formed, but with a different distribution of urethane and urea bonds as to when only diamines are used.

It should be clear that the formulae above act as examples of segmented polyurethanes and polyurethane ureas, i.e., that combinations of diol, diamine and alkanolamine extenders, and/or combinations of polyol or polyamine crosslinkers can be used to react with the diisocyanate with or without soft segment diol.

The properties of the polyurethane can be manipulated by altering the hard/soft segment ratio as well as the percentage of crosslinking used. Different definitions exist:

$$\% \ HS_{eq} = \frac{Equiv(\text{Extender}) + Equiv(Xlinker)}{Equiv(DI)} \times 100 \quad (8a)$$

Eq (8a) gives the percentage of the DI used to react with the extender (and Xlinker where applicable) to form the hard segment (HS) on an equivalence basis.

HS content is also often defined on a mass basis, in which case:

$$\% \ HS_m = \frac{Mass(DI) + Mass(\text{Extender}) + Mass(Xlinker)}{Mass(\text{total})} \times 100 \quad (8b)$$

The percentage crosslinking (% $X_{ex}$) can be defined as a percentage of the extender+crosslinker:

$$\% \ X_{ex} = \frac{Equiv(Xlinker)}{Equiv(\text{Extender}) + Equiv(Xlinker)} \times 100 \quad (9a)$$

Or, preferably as a percentage of the DI:

$$\% \ X_{DI} = \frac{Equiv(Xlinker)}{Equiv(DI)} \times 100 \quad (9b)$$

Quantities are often expressed given in equivalent weights or fractions thereof, e.g. for MDI (Molecular Mass=250.25): Equivalent weight=250.25/2=125.13 per —NCO. Thus 15.64 g of MDI is ⅛$^{th}$ of the equivalent weight.

Other (Side) Reactions:

Isocyanates form amines and $CO_2$ on contact with water; the formed amines can then react with other isocyanates. Thus all reactions must be done with dry solvents and reagents.

$$R—NCO + H_2O \rightarrow R—NH_2 + CO_2$$

Diamines can react with $CO_2$ to form ammonium carbamates (amine blooming):

$$2R—NH_2 + CO_2 \rightarrow R—NH—C(O)—O^- + {}^+NH_3—R$$

and/or with $CO_2$ and $H_2O$ in the air to form ammonium bicarbonates.

$$2R—NH_2CO_2 + H_2O \rightarrow RNH_3^+ + HCO_3^-$$

These reactions are known to those skilled in the art; care must be taken when working with these reagents to protect them from water and air. Azeotropic distillation to remove water from the reaction mixture and inert gas blankets are used to eliminate or at least limit these reactions.

Mechanical Properties are Defined as Follows:

Stress=Force/(cross-sectional) area and expressed in MPa.

Strain=(Length−original length)/original length [dimensionless] or as a percentage (for example, a strain value of 2 refers to 200% strain)

Toughness=area under the stress/strain curve [J/m$^3$=Pa]

The invention will now be described in more detail with reference to the following non-limiting examples.

EXAMPLES

List of Reagents Used in the Examples Described
Diisocyanates (OCN—R$_1$—NCO)
  4,4 Methylene diphenyl diisocyanate (MDI)
  Dimeryl diisocyanate[1] (DDI),
  2,4 and 2,6 Toluene diisocyanate (TDI)
  1,5 Naphthalene diisocyanate (NDI)
  Methylene bis toluene diisocyanate (MBTDI)
  Methylene bis(4,4-cyclohexyl isocyanate) (HMDI)
  1,4 Cyclohexane diisocyanate (CHDI),
  Isophorone diisocyanate (IPDI)
    * These are derived from dimer acids: The dimer acids as the term is used herein are described and discussed in the book "The Dimer Acids", edited by Edward C. Leonard, published by Humko Sheffield Chemical 1975. Dimer acids are the reaction product of a Diels-Alder addition or other coupling process of two aliphatic, unsaturated, predominantly 18 carbon fatty acids. Dimer acids take the form of single ring, double ring or branched chain structures predominantly having two carboxylic acid functionalities.

Oligomeric Diols (HO—R$_2$—OH)
Ether Based:
  Polytetramethylene Ether Glycol (PTMEG) (e.g. but not limited to 650, 1000 nominal MMass)
  Polyhexamethylene oxide diol (PHMO)
Hydrocarbon Based (Preferable):
  Hydroxy terminated hydrogenated polybutadiene (HPBD, e.g. Krasol HLBH-P 2000)
  Dimer diol* (DDO)
Diol Extenders (HO—R$_3$—OH)
  1,4 Butanediol (BDO)
  Ethane diol (EDO)
  Ethylene glycol
  Hexane diol (HDO)
Diamine Extenders (H$_2$N—R$_4$—NH$_2$)
  Hexamethylene diamine (NMDA)
  Ethylene diamine (EDA)
  Butane diamine (BDA)
  Trimethyl hexamethylene diamine (TMDA)
  4,4'-Methylenebis(2-chloroaniline) (MOCA)
  Dimeryl diamine
  Hydrogenated methylene dianiline (MDAH)
Polyol Crosslinkers (R$_5$—(OH)$_n$) with n=3, 4, 5 etc
  Trimethylol propane (TMP)
  Triethanolamine (TEOA)
  Pentaerythritol (PERT)
  N,N,N,N-Tetrakis(2-hydroxyethyl)ethylenediamine (THEED)
Polyamine R$_6$—(NH$_2$)$_n$ with n=3, 4, 5 Etc
  Melamine
  Diethylene Triamine
  Spermine, Spermidine
Alkanolamine extenders (H$_2$N—R$_7$—OH)
  Ethanolamine
  3-Amino-1-propanol
  4-Amino-1-butanol
  4-Amino phenol
Solvents for PU Synthesis
  The following list shows some of the solvents used in the solution polymerization reactions. In some cases single solvents are suitable as they are able to dissolve not only the starting materials, but also the reaction products. In other cases, e.g. the use of hydrocarbon soft segments, a mixture of solvents may be required to attain this goal.

Suitable solvents, which were also used as solvent combinations, are given below in Table 1.

TABLE 1

Suitable solvents

| SOLVENT | MDI | HPBD diol | BDO | HMDA | Urethane Product | Urethane\Urea Product |
|---|---|---|---|---|---|---|
| DMAc | ○ | X | ○ | ○ | ○ | X |
| DMF | ○ | X | ○ | ○ | ○ | X |
| Toluene | ○ | ○ | ○ | ○ | X | X |
| NMP | ○ | X | ○ | X | ○ | X |
| Cyclohexanone | ○ | ○ | ○ | ○(1) | ○ | X |
| MEK | ○ | X | ○ | ○(1) | X | X |
| Dioxane | ○ | X | ○ | | X | X |
| THF | ○ | ○ | ○ | ○ | | X |
| Chloroform | ○ | ○ | ○ | | | X |
| Anisole | ○ | ○ | N | N | X | X |
| Chlorobenzene | ○ | ○ | N | ○ | X | X |
| Dichlorobenzene | ○ | ○ | N | ○ | X | X |

(1) = Yellowing: Possibility of Schiff base formation between amine and ketone
X = not dissolve
○ = dissolve
N = Not determined All the solvents listed in Table 1 have been used as solvents for the synthesis of polyurethane ureas with HPBD as soft segment. No solvent on its own was sufficient to keep the polymer in solution throughout the synthesis process. The non-polar HPBD and polar urea groups are difficult to dissolve in one solvent, thus polar/non-polar solvent mixtures were tested.

The solvents were thus used in combination in certain cases, as described in the Examples below, due to the insolubility due to urea and/or HPBD in regular solvents. The mixtures tested were: anisole/NMP, chlorobenzene/NMP, ortho-dichlorobenzene/NMP, toluene/DMAc, toluene/NMP, toluene/DMF, chloroform/DMF, THF/NMP, THF/DMAc. The most successful combination proved to be ortho-dichlorobenzene/NMP.

1. Partially Crosslinked PU

In one embodiment of the invention a partially crosslinked polyurethane polymer comprising methylene diphenyl diisocyanate (MDI) and an aliphatic hydrocarbon soft segment with a butane diol (BDO) chain extender and a trifunctional amine and/or alcohol crosslinker is provided. This type of polymer is unique for medical urethanes. The partially crosslinked polymer displays a Young's modulus in the range of 4 to 15 MPa, an ultimate tensile strength of 2 to 25 MPa with a maximum strain of 350 to 600% and a toughness of 25 to 60 J/m$^3$.

The aliphatic hydrocarbon soft segment is a hydrogenated polybutadiene diol (HPBD) with a functionality of 1.9 to 2.2, preferably 1.9, and a molecular weight of 2000 to 3000, preferably 2100 or 3000, and the trifunctional crosslinker is TMP or TEAO which forms 3 to 15%, and preferably 3.75 to 10%, of the polymer (based on diisocyanate equivalents).

The partially crosslinked polymer is produced in a solvent system comprising a 4:1 mixture of toluene:DMF or a 1:1 mixture of DMAc/toluene.

The partially crosslinked polyurethane polymer has a linear elastic region in a range from 5-100%, preferably 10-60%, and more preferably 10-35%.

This embodiment pertains to adding crosslinks (of "crosslinking type 3" described above), and "titrating" to such an extent as to improve the mechanical properties of the material (in order to make it stronger, tougher or to decrease hysteresis and creep) while retaining the solubility of the polymer, in this case, without converting a gel to a liquid. The latter is important in using solution based processing (such as dip-coating and spraying) of the polymer into an article.

Example 1 (PU280)

The following example show the synthesis and mechanical properties derived by addition of crosslinks within polyurethane. The polymers comprise MDI, HPBD and BDO (extender), with the introduction of TEOA (as a crosslinker) and dibutyltin as catalyst. It is clear that the principles can also be applied to polyurethanes and polyurethane ureas containing hydrocarbon soft segments and diamine extenders.
Synthesis of Aliphatic Hydrocarbon Soft Segment Polyurethane.

The reagents are given below in Table 2. The hydrogenated polybutadiene diol (HPBD) was obtained as a sample from Nippon Soda (Japan). It has a functionality of 1.9 and a molecular weight of 3000.

TABLE 2

Reagents used in Example 1

| Reagent | Equivalents | Weight in grams |
| --- | --- | --- |
| MDI | 0.0482 | 6.031 |
| HPBD | 0.00790 | 15.079 |
| BDO | 0.0379 | 1.697 |
| TEOA | 0.00180 | 0.089 |
| DBTDL | 0.00000482 | 0.00304 |

$HS_{eq}$ = 82%

HPBD (diol) was added to a 250 ml reaction vessel followed by addition of 100 g of a 1:1 toluene/DMAc solvent system under an Ar (g) blanket. The solution was heated to 75° C. and stirred until the HPBD was fully dissolved. A Dean Stark adaptor was fitted and the solution heated to reflux. 16 g of solvent was removed to ensure removal of any residual water. The reaction was cooled to 75° C. and the MDI was subsequently added to the reaction vessel. After 30 min a clear solution of increased viscosity was obtained. The BDO and TEAO was added (in 12 g of DMAc) to the reaction mixture, followed by an additional 12 g of DMAc. The system was further reacted for 3 hours.

Films were cast (solution casting followed by evaporation drying) and tensile testing was performed on the dried films. See Table 3 below for the properties and FIG. 1 for a stress strain curve of the partially crosslinked PU.

TABLE 3

Properties of films cast from a polymer of Example 1

| Example | Young's Modulus (MPa) | 50% secant modulus | 100% secant modulus | 300% secant modulus | UTS (MPa) | Max Strain (%) | Toughness (J/m$^3$) |
| --- | --- | --- | --- | --- | --- | --- | --- |
| 1 (PU280) | 10.16 | 10.14 | 9.66 | 6.32 | 22.56 | 403 | 56.16 |

Example 2 (PU033)

The following examples show the progression of adding and increasing of the crosslinks within polyurethane. The polymers comprise MDI, HPBD and BDO (extender), with the introduction of TMP (as a crosslinker). It is clear that the principles can also be applied to polyurethanes and polyurethane ureas containing hydrocarbon soft segments and diamine extenders.

Example 2a. Synthesis of Aliphatic Hydrocarbon Soft Segment Polyurethane

The reagents are given below in Table 4. The hydrogenated polybutadiene diol (HPBD) was obtained as a sample from Cray Valley and is part of the Krasol family of products. It has a functionality of 1.9 and a molecular weight of 2100.

TABLE 4

Reagents used in Example 2a

| Reagent | Equivalents | Weight in grams |
| --- | --- | --- |
| MDI | 0.125 | 15.641 |
| HPBD | 0.0625 | 69.078 |
| BDO | 0.0625 | 2.816 |

$HS_{eq}$ = 50%

HPBD (diol) was added to a 500 ml reaction vessel containing 90 g of a 4:1 toluene:DMF solvent system and stirred until the HPBD was fully dissolved. 4,4-MDI was subsequently added to the reaction vessel which was moved to a heating mantle. After 1 hour (Temp=55-95° C.) a clear solution of increased viscosity was obtained. The BDO solution (in 38 g of the solvent system) was pipetted to the reaction mixture, followed by an additional 31 g of solvent. The system was further reacted for 1.5 hours.

Films were cast (solution casting followed by evaporation drying) and tensile testing was performed on the dried films (see Table 5 below for properties). Similar procedures were followed to produce Examples 2b and 2c, with the difference being that in Example 2b the trifunctional crosslinker TMP was added at an equivalent level of 5%, and in Example 2c at 10% relative to isocyanate (as defined in Eq 9b described above)

The mechanical properties of the three polymer examples are shown in Table 5 below. General improvement in tensile strength could be shown by increasing the crosslink density.

TABLE 5

| | Mechanical properties of polymers | | | | | | |
|---|---|---|---|---|---|---|---|
| Example | Young's Modulus (MPa) | 50% secant modulus | 100% secant modulus | 300% secant modulus | UTS (MPa) | Max Strain (%) | Toughness (J/m$^3$) |
| 2a (PU033) | 4.09 | 2.95 | 2.23 | 1.57 | 8.43 | 594 | 27.63 |
| 2b (PU035) | 6.59 | 5.78 | 4.95 | 2.89 | 9.55 | 390 | 25.15 |
| 2c (PU036) | 6.79 | 4.84 | 3.86 | 2.65 | 12.16 | 490 | 33.10 |

Example 3 (PU206, PU217, PU216, PU215 and PU211

The following examples also show the progression of adding and increasing crosslinks in a polyurethane but with regard to the improvement in hysteresis. The polymers comprise MDI, PTMEG and BDO (extender), with the introduction of TEOA (as crosslinker). It is clear that the principles can also be applied to polyurethanes and polyurethane ureas containing hydrocarbon soft segments and diamine extenders.

Example 3a Synthesis of a PTMEG Soft Segment Polyurethane (PU206)

The reagents for the synthesis are given below in Table 6. The PTMEG was obtained from Sigma Aldrich (Cat #345288; CAS: 25190-06-1), it has a functionality of 2 and a nominal molecular weight of 650.

TABLE 6

| Reagents used in Example 3a | | |
|---|---|---|
| Reagent | Equivalents | Weight in grams |
| MDI | 0.0803 | 10.047 |
| PTMEG | 0.0382 | 12.428 |
| BDO | 0.0382 | 1.724 |

HS$_{eq}$ = 48%

PTMEG together with 111 g DMAc solvent was added to a 250 mL reaction vessel and stirred until the PTMEG was fully dissolved. The reaction was heated to 65° C. and MDI (in 10 g DMAc) was subsequently added to the reaction vessel. After 5 min the reaction was further heated to 75° C. After 1 hour a clear solution of increased viscosity was obtained. The BDO solution (in 10 g DMAc) was added to the reaction mixture and further reacted for 1.5 hours.

Figure 2:
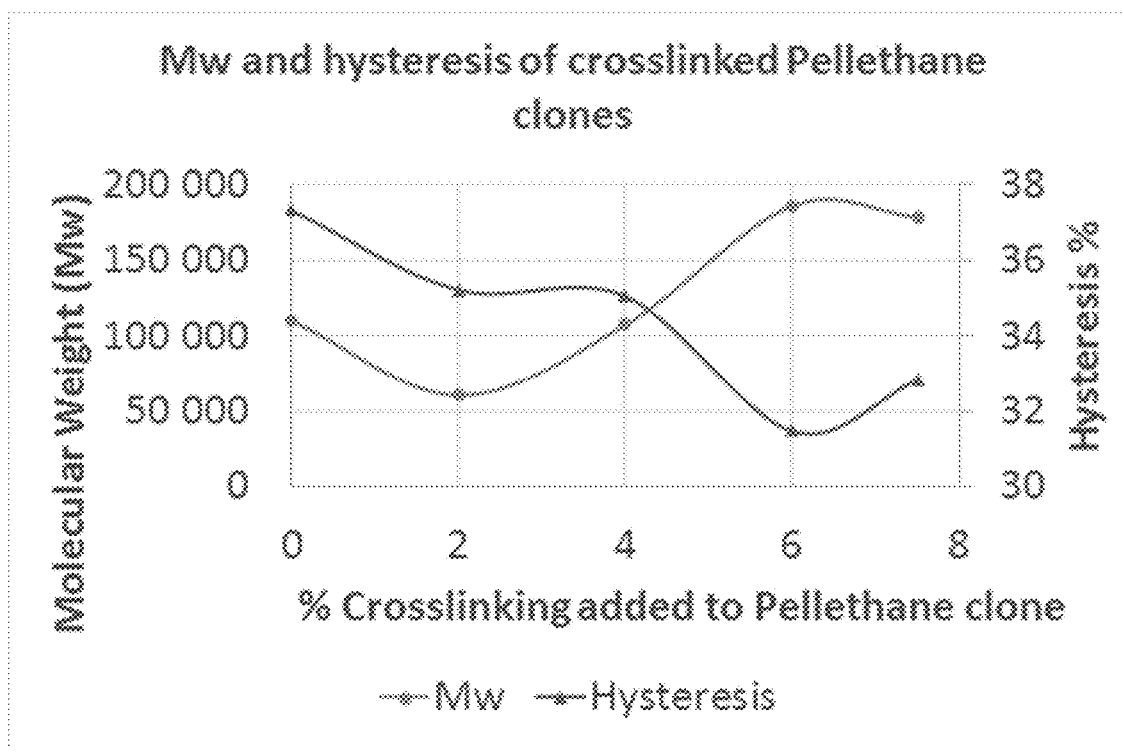
FIG. 2 is a graph showing the change in hysteresis and molecular weight of a PTMEG soft segment polyurethane with increasing crosslinking (Example 3a)

Films were cast (solution casting followed by evaporation drying) followed by molecular weight and hysteresis testing (see FIG. 2).

A similar procedure was followed to produce Examples 3b-3e, where 3b-3e contain 2%, 4%, 6% and 7.5% of the trifunctional crosslinker TEOA, respectively, relative to isocyanate (as defined in Eq 9b above).

The change in hysteresis (triangle) and molecular weight of the polymers are shown in FIG. 2. An improvement of ~17% in hysteresis was observed with a crosslinking of 6%. However, in general a decrease in hysteresis was observed with increasing crosslinking with an increase in molecular weight (circle), as expected.

Interestingly, sample 3e which contained 7.5% crosslinker gelled a day after the reaction was complete. The gelation could be reversed by incubation of the polymer gel at 110° C. for 24 hours.

1A. Oxidative Stability of Hydrocarbon Soft Segment Polyurethanes

In this embodiment of the invention there is provided, for example, a polyurethane comprising a MDI (diisocyanate), HPBD (diol) as soft segment and BDO as chain extender subjected to oxidative stress in order to show the oxidative stability of polyurethane containing hydrocarbon soft segments.

Example 4 Oxidative Stress Ageing Study

Figure 3:
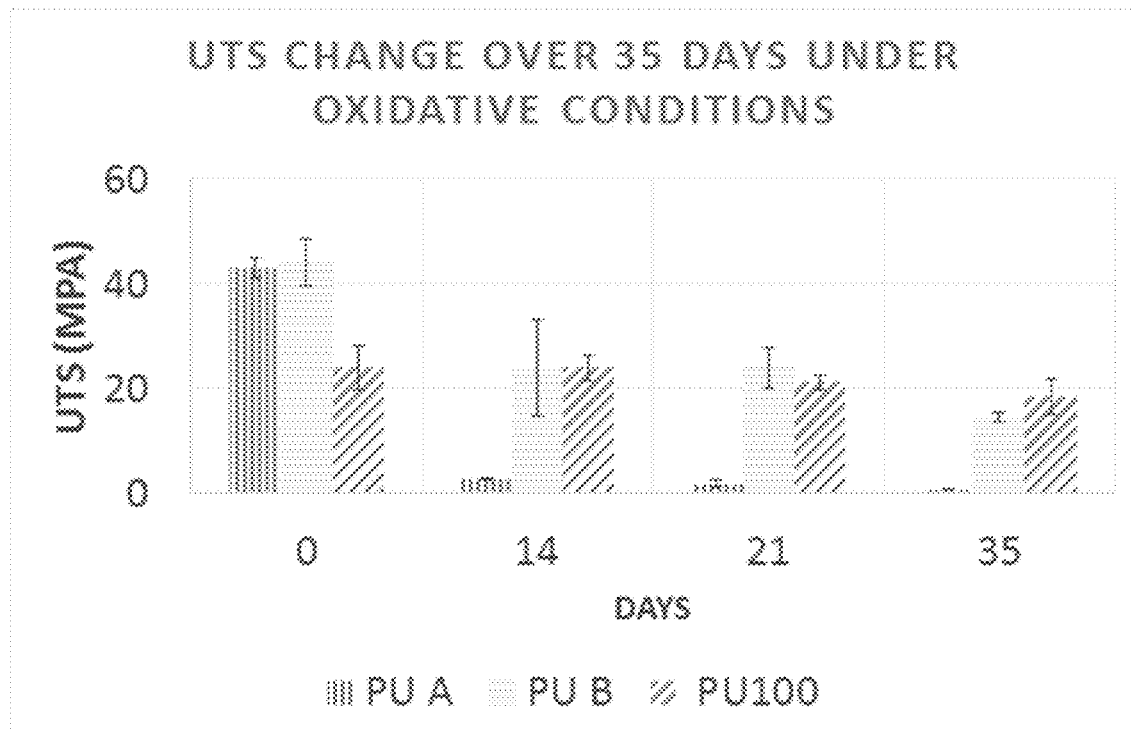
FIG. 3 is a graph showing changes in Ultimate Tensile Strength under oxidative conditions of a synthesised polymer with an aliphatic hydrocarbon soft segment (PU 100) and commercial control polyurethanes, PU A (polyether soft segment) and PU B (polycarbonate with 20% siloxanes as soft segment) (Example 4)

The polyurethane consisting of MDI, HPBD (diol) and BDO as extender was synthesized in the two-step process at 75° C. (PU100—aliphatic hydrocarbon soft segment), as described in Example 6, below. Films were cast of the synthesized polymer as in Example 3, as well as two commercial polyurethanes that serve as control samples (PU A—polyether soft segment; PU B—polycarbonate with 20% siloxanes as soft segment). Dogbones were cut from the films and subjected to an aggressive oxidative study: 0.1M AgNO$_3$, at 90° C. for 35 days. The samples were removed at 7, 14, 21 and 35 days to be analyzed by tensile testing. The results show that the polymer synthesized containing HPBD (PU100) as described above is resistant to oxidative degradation, where the commercial standards, PU A and PU B do undergo degradation as shown in FIG. 3. PU A degrades completely as expected, whilst PU B undergoes some initial degradation but then retains some stability.

Example 5 Oxidative Stress Ageing Study #2

Figure 4:
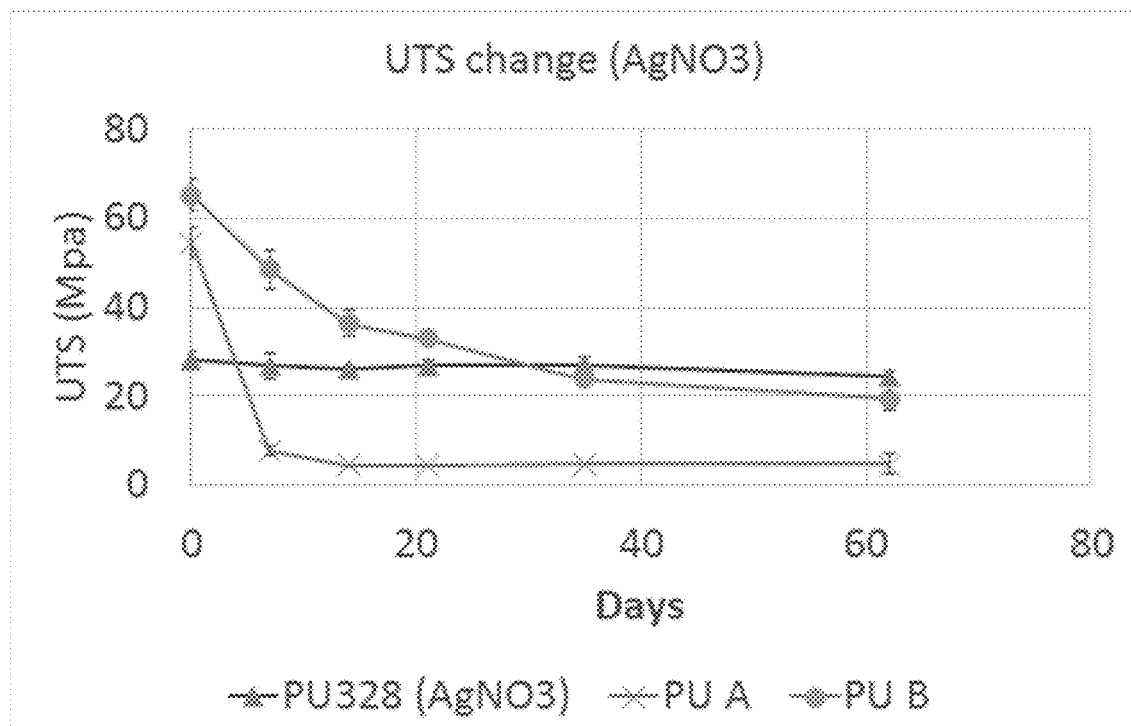
FIG. 4 is a graph showing in Ultimate Tensile Strength (UTS) under oxidative conditions of PU328 and commercial controls, PU A and PU B (Example 5)
Figure 5:
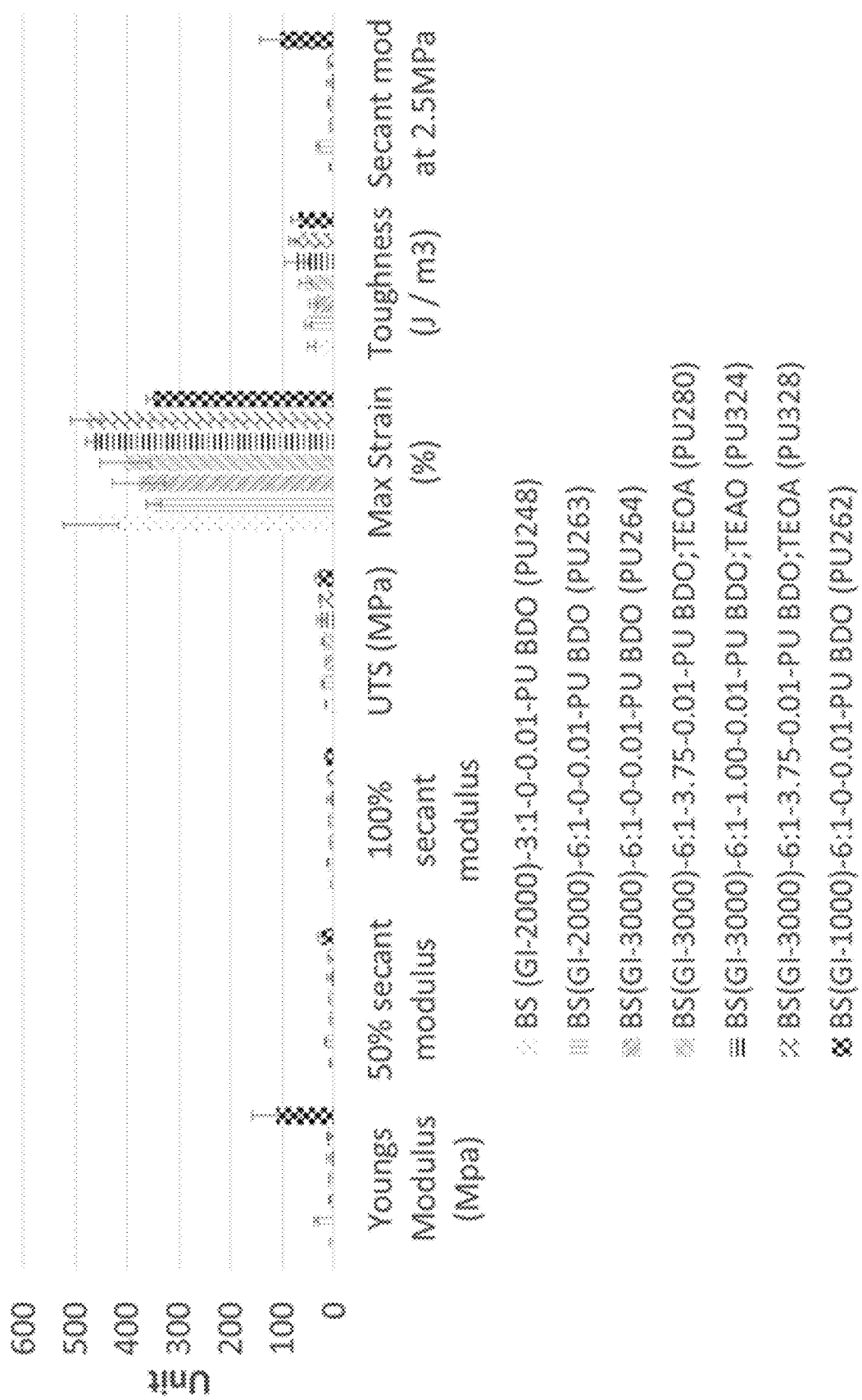
FIG. 5 is a graph illustrating the mechanical properties of different PU compositions having different aliphatic soft segments.
Figure 6:
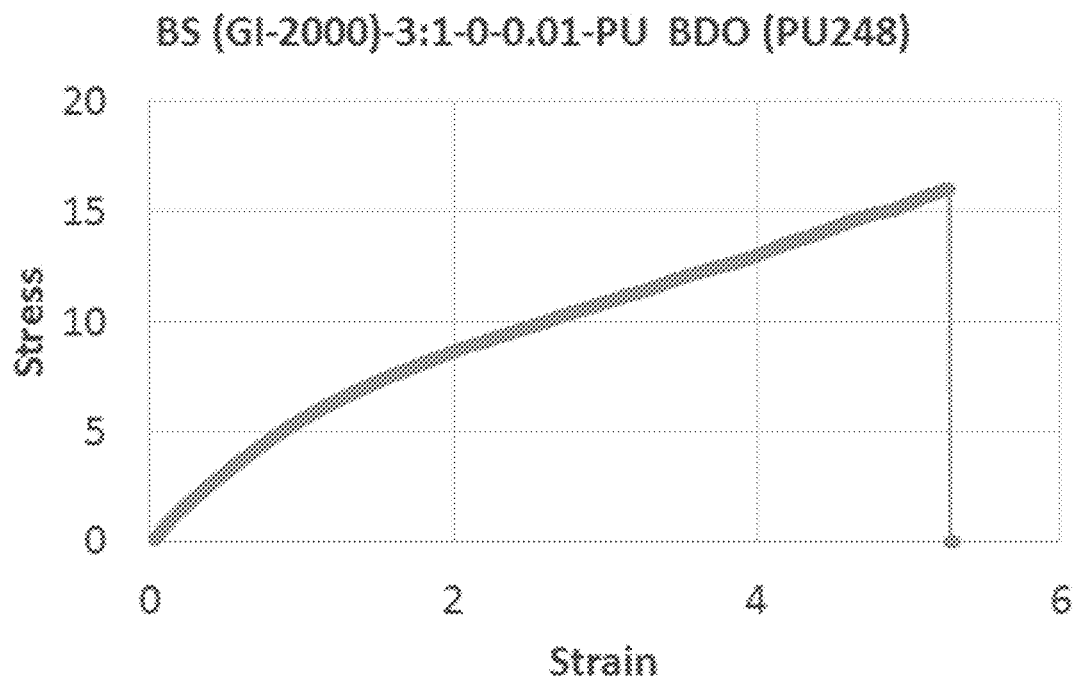
FIG. 6 is a stress strain graph of sample BS-(GI-2000)-3:1-0-0.01-PU BDO (PU248)
Figure 7:
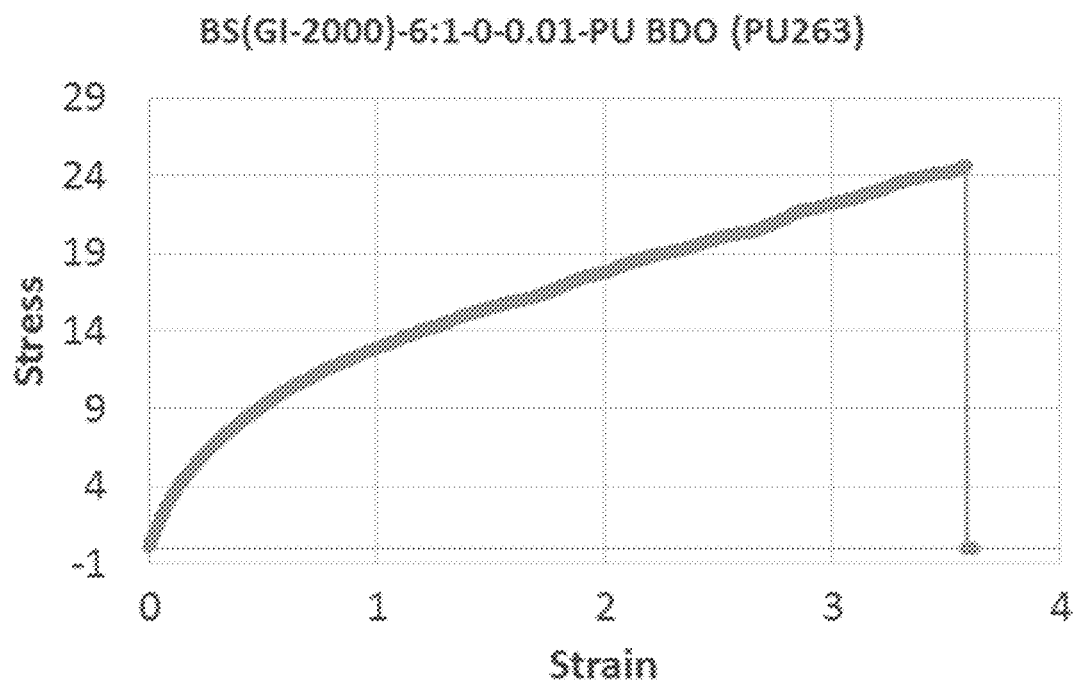
FIG. 7 is a stress strain graph of sample BS-(GI-2000)-6:1-0-0.01-PU BDO (PU263)
Figure 8:
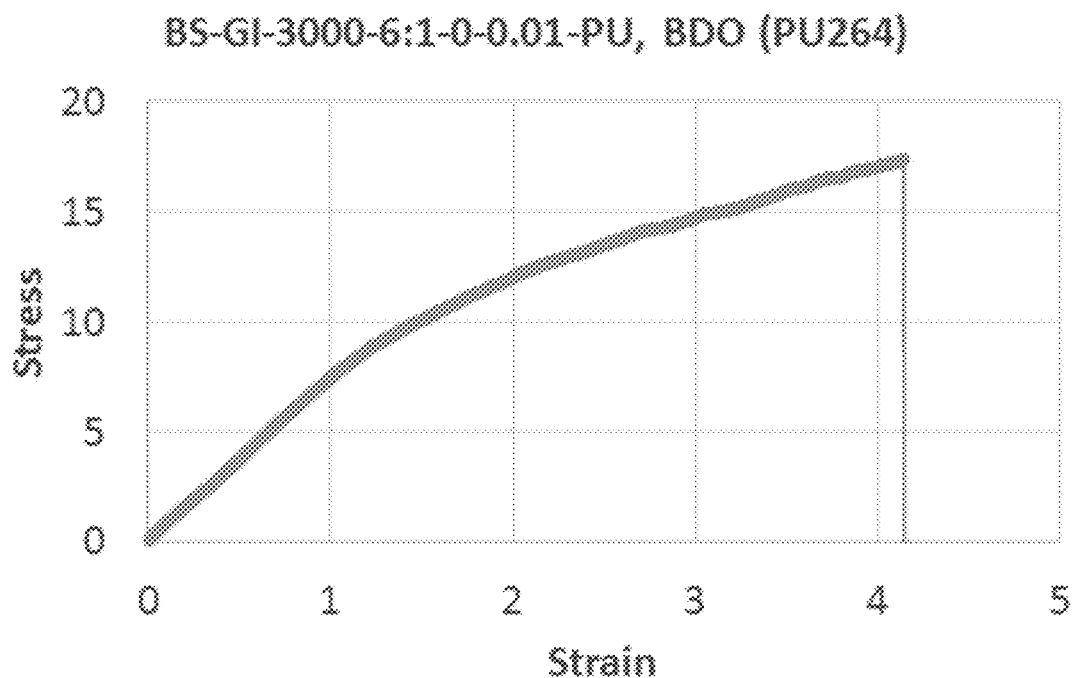
FIG. 8 is a stress strain graph of sample BS-(GI-3000)-6:1-0-0.01-PU BDO (PU264)
Figure 9:
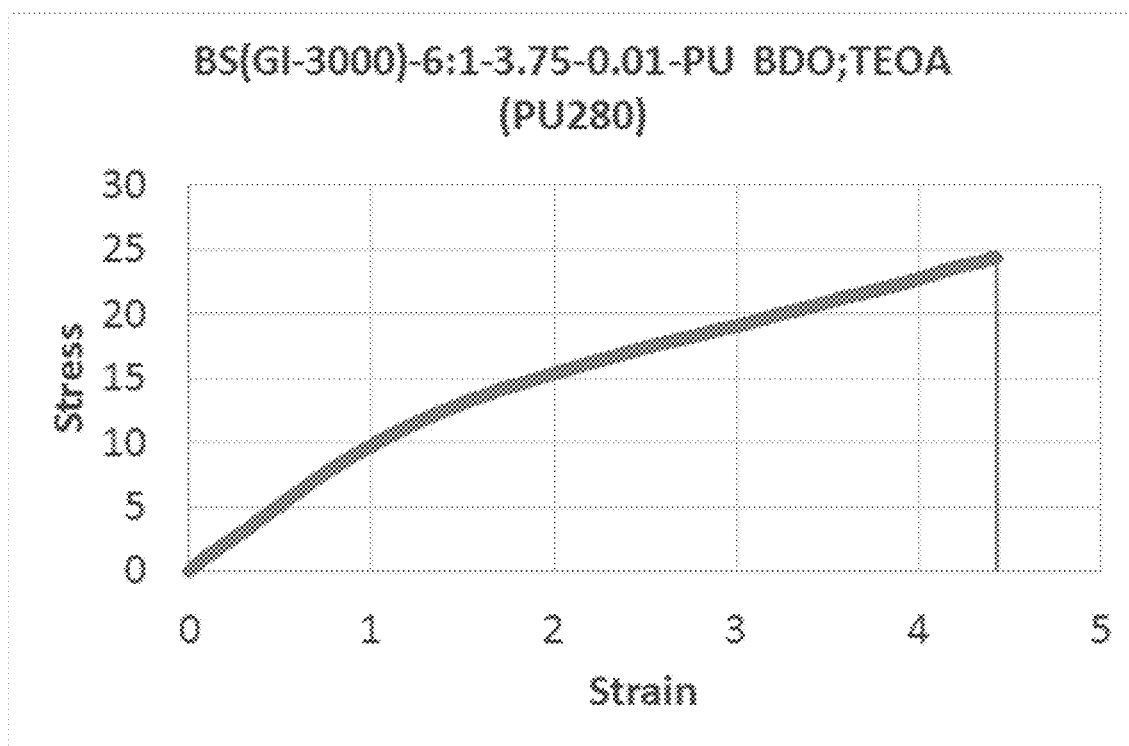
FIG. 9 is a stress strain graph of sample BS-(GI-3000)-6:1-3.75-0.01-PU BDO; TEOA (PU280)
Figure 10:
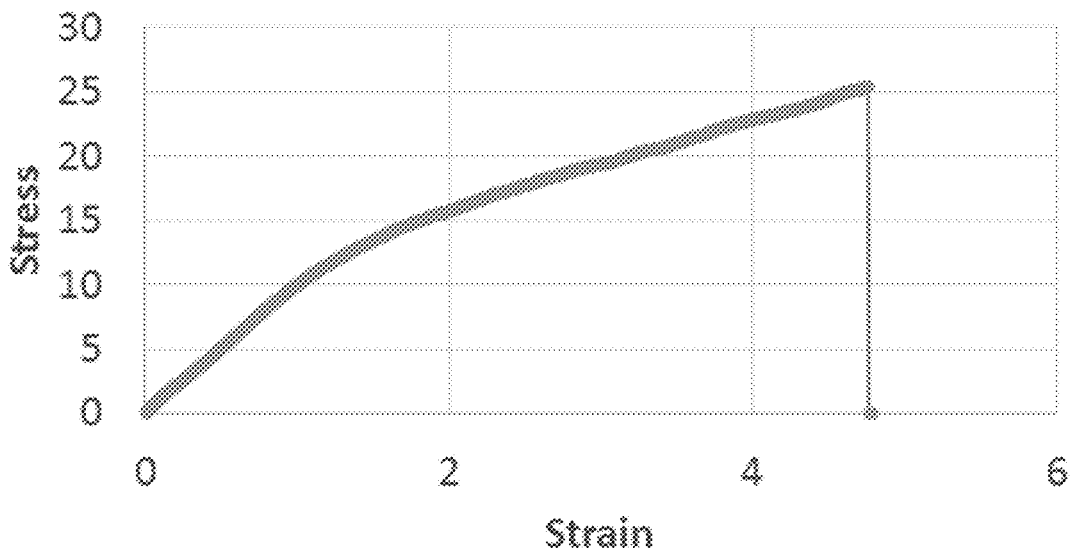
FIG. 10 is a stress strain graph of sample BS-(GI-3000)-6:1-1.00-0.01-PU BDO; TEAO (PU324)
Figure 11:
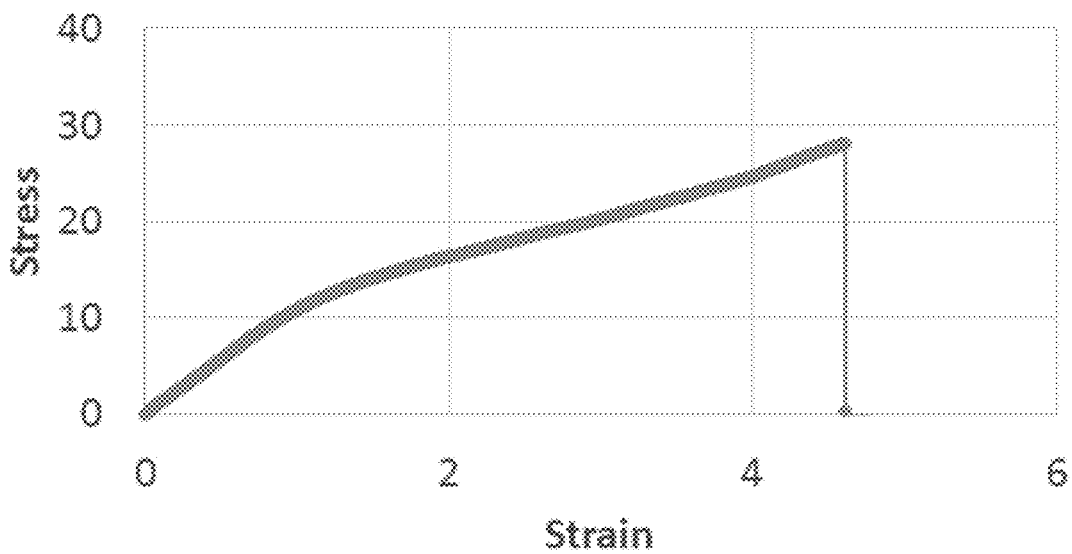
FIG. 11 is a stress strain graph of sample BS-(GI-3000)-6:1-3.75-0.01-PU BDO; TEAO (PU328)
Figure 12:
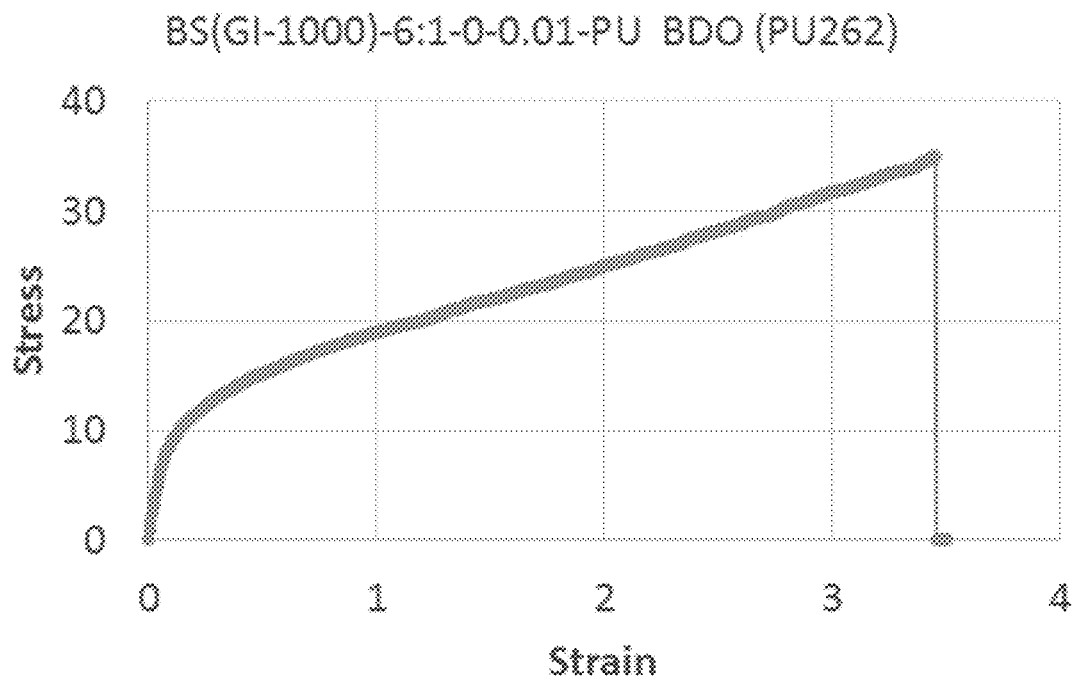
FIG. 12 is a stress strain graph of sample BS-(GI-1000)-6:1-0-0.01-PU BDO (PU262).

The polyurethane synthesized according to the formulation and method of Example 1 was also subjected to an oxidation study under the same conditions and controls as described in Example 4. As is evident from the results (shown in FIG. 4), the polyurethane containing HPBD-diol as soft segment is oxidatively stable even with a different composition with regards to crosslink density and the ratio of hard segment to soft segment. An ANOVA analysis and a t-test were carried out on the results obtained from the oxidation study and the results show that for the polyurethane containing HPBD-diol, there was no statistically-significant change in the UTS between day 0 and day 62 (p-value=0.186 (ANOVA). The corresponding values for PU B show that there was a ~70% decrease in UTS between day 0 and day 62 (p-value=1.45E-05 (ANOVA) 3.26E-05 (t-test). This result demonstrates the enhanced durability of the polyurethane containing HPBD-diol relative to the control polyurethane.

1B. Mechanical Property Range of Polyurethanes with an Aliphatic Hydrocarbon Soft Segment as in this patent In further embodiments of the invention a polyurethane polymer comprising methylene diphenyl diisocyanate (MDI) and an aliphatic hydrocarbon soft segment (HPBD-diol) with a butane diol (BDO) chain extender is provided.

The embodiments may or may not contain a trifunctional alcohol as crosslinker and dibutyltin as catalyst (see legend key to follow). This type of polymer is unique for medical urethanes. The partially crosslinked polymer displays a Young's modulus in the range of 4 to 110 MPa, an ultimate tensile strength of 8 to 30 MPa with a maximum strain of 348 to 594% and a toughness of 40 to 77 J/m$^3$ All these polyurethanes was synthesized according to the two-step method as described in Example 1 with the appropriate reagents and stoichiometry, and the results are shown in FIGS. 5 to 12.

Legend Key:
- BS (GI-#)=Mw of the Soft segment i.e., 1000, 2000 or 3000
- 6:1 or 3:1=Ratio of MDI to HPBD-diol
- 0 or 1.00 or 3.75=percentage of crosslinking as Equivalent of HS
- 0 or 0.01=if catalyst was used or not and percentage thereof as Equivalent of HS
- BDO=chain extender used
- TEOA=crosslinker used 2. Hydrocarbon Soft Segments In a further embodiment of the invention a polyurethane formed by reacting hydrogenated polybutadiene diol as an aliphatic, hydrocarbon soft segment with MDI in a two-step process is described. The reaction is carried out in 1:1 ratio of ortho-dichlorobenzene and N-methyl-2-pyrrolidone (in a ratio of 5.8:4.2). This is followed by the addition of hexamethylene diamine (HMDA) dissolved in a 1:1 mixture of the ortho-dichlorobenzene/NMP solvent system. The polymer formed has an ultimate tensile strength of 18 MPa with a 50% secant modulus of 4.7 MPa.

Polyurethanes were historically made from soft segments that contain ester and ether groups that are respectively hydrolytically and oxidatively unstable in vivo. More recent urethanes containing soft segments with carbonate or siloxane groups have been claimed to be stable, but there is evidence that they are also susceptible to hydrolytic degradation.

The use of purely, essentially saturated, hydrocarbon soft segments will result in polymers with improved hydrolytic and oxidative stability. As shown in Examples 1, 2 and 3 above, by titrating the amount of crosslinking to the PU an improvement in the strength, toughness and hysteresis of the PU can be achieved. Additionally, the use of urea in the formation of the PU will also result in the improvement of mechanical properties, and possibly result in thermally convertible gels, such as in Examples 1 and 3.

Example 6 (PU044)

This polyurethane formulation was made using an aliphatic soft segment. The soft segment is a hydrogenated polybutadiene diol (HPBD, Cray Valley; 2100 mol mass). The reaction was done in a two-step process in ortho-dichlorobenzene and N-methyl-2-pyrrolidone. The raw materials used are given in Table 7 below. All the materials were obtained from Sigma Aldrich, except the HPBD (Cray Valley). The MDI was distilled before use.

TABLE 7

Reagents used in Example 6

| Reagent | Equivalent weight | Weight in grams |
|---------|-------------------|-----------------|
| MDI     | 0.03125           | 3.910           |
| HPBD    | 0.01562           | 17.170          |
| HMDA    | 0.01562           | 0.908           |

$HS_{eq}$ = 50%

HTPB and 62 g of solvent (58:42, dichlorobenzene:NMP) were added to the reaction vessel, and stirred until homogenous. MDI was added to the solution which was stirred for 80 minutes without heating and a further 20 minutes at 60° C. The HMDA was dissolved in 60 g of solvent (50/50 dichlorobenzene/NMP) and added dropwise to the stirring reaction mixture. A clear solution resulted.

Figure 13:
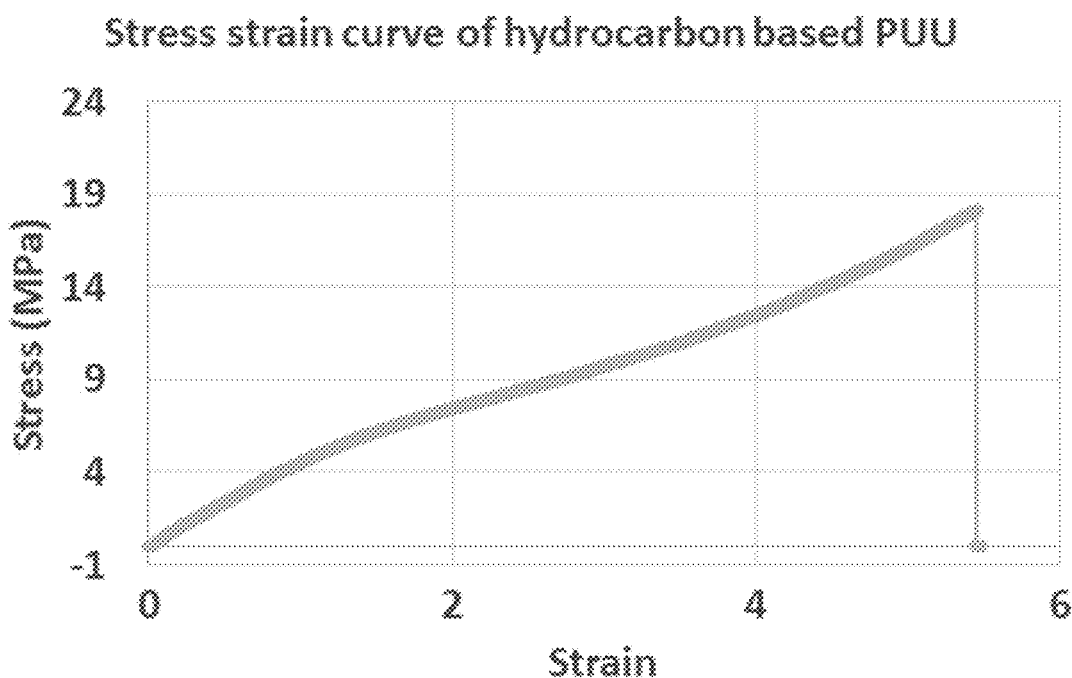
FIG. 13 is a stress strain graph of a hydrocarbon-based polyurethane formulation made using an aliphatic soft segment (Example 6)

Films were cast on Mylar sheets 3 hours after HMDA addition. The films were dried at 60° C. overnight and dogbone samples were cut using an ASTM 1708 die. The stress strain graph is as FIG. 13. The ultimate tensile strength (UTS) was 18.1 Mpa with a 50% secant modulus of 4.7 MPa.

3. Use of Alkanolamines as Chain Extenders

In this embodiment of the invention there is provided, for example, a polyurethane urea comprising a MDI (diisocyanate), HPBD (diol) as soft segment and 4-amino-1-butanol as chain extender to show improved strength over a PU which has BDO as chain extender.

Example 7 Alkanolamine (4-amino-1-butanol) as chain extender (PU231)

The polyurethane consisting of MDI, HPBD (diol) and 4-amino-1-butanol as extender was synthesized in the two-step process at 75° C. as described in Example 1 according to the formulation given in Table 8 below. This can also be done in a one-step process.

TABLE 8

Reagents used in Example 7

| Reagent         | Eq      | Weight (g) |
|-----------------|---------|------------|
| MDI             | 0.0135  | 1.694      |
| HPBD (diol)     | 0.00436 | 5.138      |
| 4-amino-1-butanol | 0.00872 | 0.389    |

$HS_{eq}$ = 65%

Films were cast on glass petri dishes 24 hours after 4-amino-1-butanol addition. The films were dried at 75° C. overnight and dogbone samples were cut using an ASTM 1708 die. The tensile data is shown below (Table 9) and compared to a PU synthesized with BDO as chain extender (2a). Clearly, an increase in UTS is observed with the use of the alkanolamine as chain extender.

TABLE 9

Mechanical properties of polymers

| Example | Young's Modulus (MPa) | 50% secant modulus | 100% secant modulus | 300% secant modulus | UTS (MPa) | Max Strain (%) | Toughness (J/m$^3$) |
|---|---|---|---|---|---|---|---|
| 2a (PU033) | 4.09 | 2.95 | 2.23 | 1.57 | 8.43 | 594 | 27.63 |
| 5 (PU231) | 17.18 | 9.26 | 7.77 |  | 11.32 | 235 | 17.83 |

4. Convertible Gelation

In a further embodiment of the invention there is provided a polyurethane polymer having a thermally convertible gel formulation which may be converted to a liquid formulation by extended heating. This renders the polymer suitable for solvent processing techniques such as casting, spraying and spinning. The polymer has an ultimate tensile strength of 20 to 60 MPa (preferably 33.7 MPa) and a Young's modulus of 10 to 90 MPa (preferably 86.3 MPa).

The conversion of the gel to the liquid may be done at a temperature range of 90-125° C. (preferably around 120° C.). The polymer may be formed by a one or two-step process and may be formed using a diamine, triol, triamine or insolubilizing chain extender.

Example 8 (PU021)

A polyurethane urea was synthesized using the two-step process as described previously, and according to the formulation given in Table 10 below.

The reaction was performed without external heating. The reaction solution (in DMAc), which gelled after addition of HMDA, was subsequently heated overnight at 120° C. The heating resulted in a gel-free solution even when cooled to room temperature from which samples were cast for mechanical evaluation.

The ultimate tensile strength of the PUU was 33.7 MPa with a Young's modulus of 86.3 MPa.

TABLE 10

Reagents used in Example 8

| Reagent | Eq | Weight (g) |
|---|---|---|
| MDI | 0.125 | 15.64 |
| Dimer Diol | 0.1042 | 28.24 |
| HMDA | 0.0208 | 1.21 |

Figure 14:
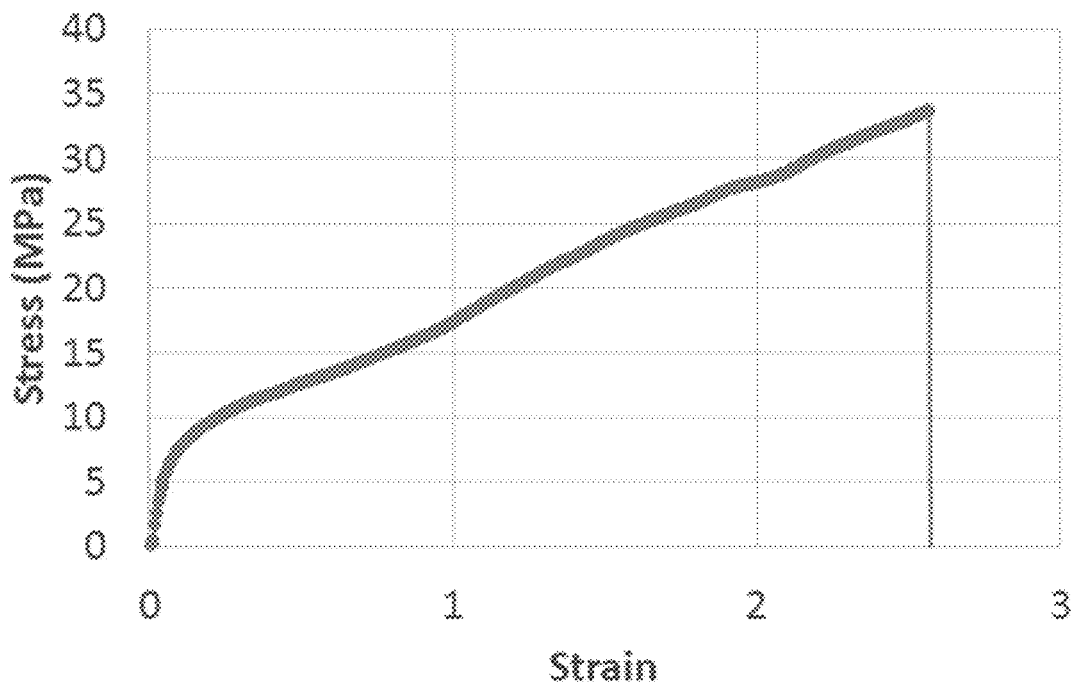
FIG. 14 is a stress strain graph of a polyurethane urea (PUU) synthesised using a two-step process (Example 8)

As shown in the stress strain graph (FIG. 14), the polymer did not have a well-defined yield point.

Example 9 (PU015b

This partially crosslinked polyurethane urea was synthesized with the two-step process at 55° C. (formulation in Table 11 below). The solution gelled 2 days after synthesis, at which point it was heated at 120° C. overnight. The solution returned to a stable liquid phase at room temperature and films were cast. The ultimate tensile strength of the polymer was 26.45 MPa with a Young's modulus of 16.80 MPa.

TABLE 11

Reagents used in Example 9

| Reagent | Eq | Weight (g) |
|---|---|---|
| MDI | 0.125 | 15.64 |
| PTMEG | 0.05625 | 18.281 |
| MOCA | 0.05 | 6.904 |
| HMDA | 0.0125 | 0.726 |
| TEOA | 0.00625 | 0.311 |

$HS_{eq} = 55\%$ (see also Examples 3e and 8)

5. Living Hinge Polymer

In another embodiment of the invention, a living hinge polyurethane polymer comprising methylene diphenyl diisocyanate (MDI) and a dimer diol. The polymer has a defined yield point in the range of 10-40 MPa, preferably 20-30 MPa at a strain of 1-10%, preferably 3-7% with an ultimate tensile strength of 20-60 MPa, preferably 30-60 MPa (e.g. 38.8 MPa, at 74% strain) to 40-70 MPa (at 390% strain) and a Young's modulus in the range of 90 MPa to 700 MPa is provided.

The living hinge polymer, when crosslinked with a tri- or higher polyol, or through allophanates and/or biurets, has a hard to soft segment ratio of 20 to 80%, preferably 30-70% and more preferably 40-60% (based on equivalents) and a crosslinking of 0-25%, preferably 5-20%, more preferably 5-15% (based on diisocyanate equivalents).

The living hinge polymer may be synthesized in a one step process (for homopolymers) or a two-step process. In the two-step process a suitable solvent may be used. Suitable solvents may be selected from, but not limited to, dimethyl acetamide (DMAc), toluene, dimethylformamide (DMF), ortho-dichlorodibenzene, N-methyl-2-pyrrolidone (NMP), methyl ethyl ketone (MEK), dioxane and suitable mixtures thereof. A preferred solvent is DMAc, or a solvent system comprising ortho-dichlorobenzene/NMP or toluene/DMF.

The stoichiometry of the reaction is selected such that all reactive isocyanate (NCO) groups are reacted with dimer diol (Part A). In addition, the polyurethane may optionally be formed from further diamine or diol chain extenders and/or crosslinkers (Part B). In this case, the stoichiometry is selected that Part A and Part B reacts with all isocyanate groups.

In this embodiment of the invention, and in one example described below, the living hinge polyurethane polymer in solvent is capable of being thermally reversed from a gel to a liquid. It should, however, be noted that gel conversion does not imply living hinge characteristic or vice versa but, as described in an example below, the gel conversion and living hinge properties can occur in one polymer.

The living hinge polymer described below is the type of polyurethane that has a well-defined yield point beyond its elastic limit. Depending on the specific reactants and formulation used, it may be achieved with either a segmented or non-segmented polyurethane. Both solution and bulk polymerization can be used to obtain these polymers.

Such materials are useful in heart valves and many other applications where repeated flexing is required. The polymer can be used to manufacture a heart valve with a living hinge at the base of the heart valve cusps. It should be noted that flex fatigue resistance is enhanced by alignment of the polymer chains beyond the yield point defined as an increase in strain without a corresponding increase in stress. This is accompanied by a necking down and molecular alignment at the flex location to form the hinge. A key requirement is for the polymer to possess an acceptable yield point.

The desired property of living hinge systems, namely their high flex fatigue resistance at the hinge point, results from the aligning of the polymer chains across the hinge line.

Example 10 (PU017)

Solution Polymerization

In this example, the polymer formed exhibits the following properties:
Partial crosslinking;
Thermally convertible gelation; and
Is a polyurethane urea (PUU) as HMDA and MOCA was used, which, in combination with urea formation, was probably responsible for the thermally convertible gelation Polyurethane urea was made using solvent-based two-step polyurethane synthesis method. The solvent used in this experiment was dimethyl acetamide (DMAc) (Sigma Aldrich) that was azeotropically dried (by distilling added toluene under reduced pressure prior to use). The reactants used were stoichiometrically calculated to ensure that all of the reactive NCO moieties were reacted. The raw materials used are given below in Table 12. All the materials were obtained from Sigma Aldrich, except the Dimer Diol (Croda). The MDI was distilled before use and the TEOA and HMDA were dried over 3 Å molecular sieves.

TABLE 12

Reagents used in Example 10

| Reagent | Equivalents | Weight in grams |
|---|---|---|
| MDI | 0.125 | 15.641 |
| Dimer Diol | 0.05625 | 15.244 |
| MOCA | 0.05 | 6.904 |
| HMDA | 0.0125 | 0.726 |
| TEOA | 0.00875 | 0.4354 |

$HS_{eq}$ = 57%; $X_{eq}$ = 7%

The reaction was performed in a 500 ml round-bottom flask in a heating mantle. All additions were performed under constant nitrogen flow. After addition of the solvent and the MOCA, the dimer diol was added and the solution was shaken to achieve homogeneity. After addition of the MDI, the solution was heated to 60° C. and stirred for 1 hour. The HMDA and TEOA were subsequently dissolved in DMAc and added over 30 seconds. Gel particles formed and a 2-phase system was obtained. The solution was heated overnight at 120° C., which resulted in the conversion of the gel to a liquid state even when cooled to room temperature.

Figure 15:
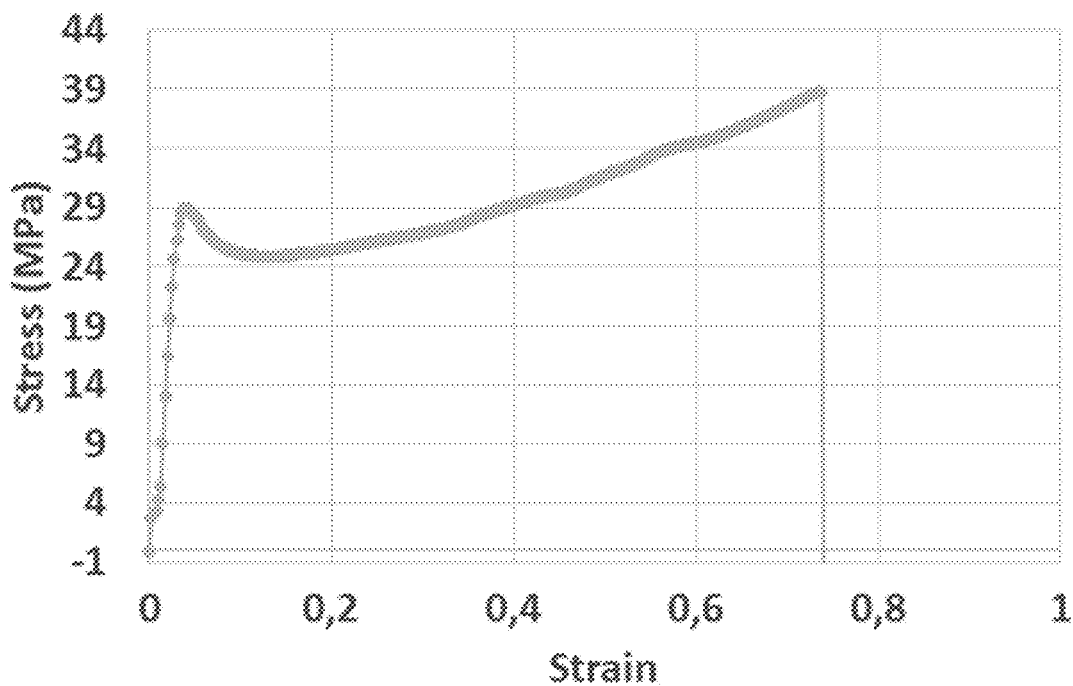
FIG. 15 is a stress strain graph of a sample prepared from the reaction of a polyurethane urea made using a solvent-based two-step polyurethane synthesis method (Example 10)

Samples were cast and left to dry at 60° C. overnight and dogbone specimens were cut using an ASTM D1708 cutter. The stress strain graph is shown in FIG. 15. The polymer showed a yield point at (4% strain; 29 MPa), UTS was 38.8 MPa (at 0.74 (or 74%) strain) with an initial Young's modulus of 678 MPa.

Example 11

Homopolymer Bulk Polymerization

A homopolymer (only dimer diol+MDI) was synthesized in bulk by a 1 step process. The synthesis was performed by adding a stoichiometric amount of MDI to dimer diol in a 1:1 ratio. The two reactants were mixed by hand in a beaker. The solution turned white and thickened rapidly. After 4 hours of reaction the resulting polymer was cut into small pieces and heat compression moulded at 180° C. into films.

Figure 16:
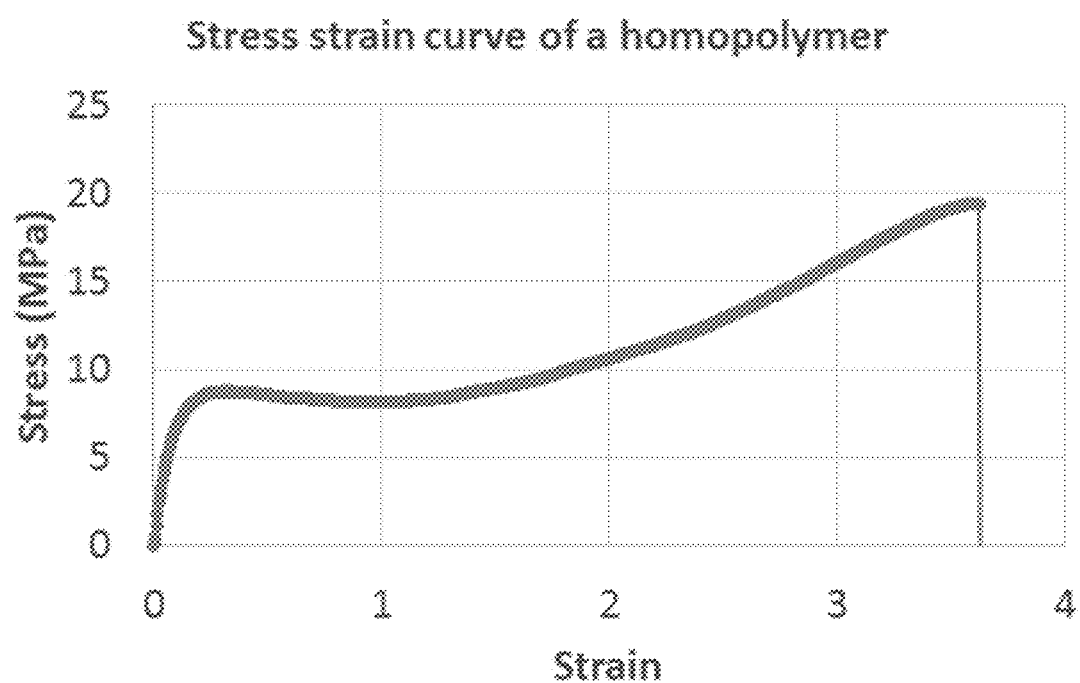
FIG. 16 is a stress strain graph of a sample prepared from a homo-polymer bulk polymerisation synthesis by a one-step process (Example 11)

Dog bone specimens (ASTM 1708) were then cut for tensile testing. As shown in the stress strain graph (FIG. 16), an ultimate tensile strength of 63.8 MPa (at 390% strain) was achieved with a Young's modulus of 90 MPa (secant modulus, 29 MPa; 30% elongation). Dissolving the film in DMAc proved difficult.

6. PU/Silicone IPNs

Interpenetrating polymer networks (IPNs) are networks of two (or more) polymers that are individually crosslinked and occupy the same volume but are not chemically linked to each other. The entanglement is physical, and cannot be separated without breaking chemical bonds. Semi-IPNs are similar, but with the distinction that in SIPNs only one of the polymers is crosslinked.

7. Reaction Injection Molded (RIM) Polyurethane Heart Valves

In this embodiment of the invention there is provided, for example, a reaction injection moulded (RIM) polyurethane comprising a MDI (diisocyanate) and a combination of PTMEG forming a first component, and BDO and TMP or oligomeric diol or polyol with extenders and crosslinkers forming a second component. The MDI may be optionally mixed with catalysts, plasticizers, bulking agents and/diluents.

The PTMEG and MDI are mixed at a reaction temperature of 50° C. to form a prepolymer, and the prepolymer is blended with a mixture of BDO and TMP and injected into and reacted in a mould to form the formed valve product.

Reaction injection moulding (RIM) is a process whereby 2 (A and B) or more reactants that are kept separately are injected through a mixing device into a mould cavity.

After reaction and solidification, the moulded part is removed from the mould. RIM is generally used to make crosslinked parts, but formulations that produce linear polymers are not excluded. Reagents are generally used in bulk and not in solution.

All the structure/property principles such as using hydrocarbon soft segments and urea groups to improve properties of the material apply but compositions may differ in degree of crosslinking from solution-based formulations as the RIM materials are often intended to be highly crosslinked.

RIM can also be performed by admixing all the components and then injecting the reaction mixture into a mould, as below.

Example 12

Polyurethane based on PTMEG, MDI, BDO and TMP was used as the material for the RIM process (see Table 13 below). The reaction was performed using in a two-step method in bulk. PTMEG and MDI were added to a flask and reacted at 50° C. for 40 minutes. BDO and TMP were mixed together and added to the pre-polymer with mixing. The mixture was placed in a vacuum oven (at 25° C.) for 4 minutes for degassing and aspirated into a syringe. The polyurethane was then injected into the valve mould. A crosslinked polyurethane product was obtained.

TABLE 13

Reagents used in Example 12

| Reagent | Eq | Weight (g) |
|---------|--------|------------|
| MDI | 0.125 | 15.63 |
| PTMEG | 0.065 | 20.96 |
| BDO | 0.0733 | 2.934 |
| TMP | 0.0073 | 0.326 |

$HS_{eq} = 64\%$; $X_{eq} = 5.84\%$

Note:

The terms Mass and Weight are used interchangeably in this document, and indicated mass in grams.

The term molecular weight is also often used for molecular mass (g/mol).

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

What is claimed is:

1. A medical implant device comprising a partially crosslinked polyurethane polymer made from reacting methylene diphenyl diisocyanate (MDI) and a hydrogenated polybutadiene diol (HPBD) soft segment having a functionality of 1.9 to 2.2 and a number average molecular weight of ~1000-3000; said polymer comprising a chain extender, which is selected from one or more of a diamine, an alkanolamine, 1,4-butane diol (BDO), ethane diol (EDO), ethylene glycol, and hexane diol (HDO); said polymer further comprising a crosslinker; and said polymer having a linear elastic region in a range from 5 to 100%.

2. A medical implant device as claimed in claim 1, wherein the chain extender comprises a diol selected from one or more of 1,4-butane diol (BDO), ethane diol (EDO), ethylene glycol, and hexane diol (HDO).

3. A medical implant device as claimed in claim 1, wherein the crosslinker is selected from either or both of triethanolamine (TEOA) and trimethylol propane (TMP) in the range of 3 to 15% of the polymer (based on diisocyanate equivalents).

4. The medical implant device as claimed in claim 1 wherein the chain extender comprises a diamine selected from the group consisting of hexamethylene diamine (HMDA), ethylene diamine (EDA), butane diamine (BDA), trimethyl hexamethylene diamine (TMDA), 4,4'-methylenebis(2-chloroaniline) (MOCA), dimeryl diamine and hydrogenated methylene dianiline (MDAH).

5. A medical implant device as claimed in claim 1, wherein the chain extender comprises a diamine.

6. The medical implant device as claimed in claim 1, wherein the chain extender comprises an alkanolamine selected from the group comprising ethanolamine, 3-amino-1-propanol, 4-amino-1-butanol and 4-amino-phenol.

7. The medical implant device as claimed in claim 6 which is formed by a one or two-step process.

8. The medical implant device as claimed in claim 6 which further includes a crosslinker selected from the group comprising a multifunctional amine and an alcohol crosslinker.

9. A medical implant device as claimed in claim 1, having a thermally convertible gel formulation which is converted to a liquid formulation by extended heating to render the polymer suitable for solvent processing techniques.

10. The medical implant device as claimed in claim 9, wherein the conversion of the gel to the liquid is achieved at a temperature range of 90-125° C.

* * * * *